United States Patent [19]
Wheeler

[11] 3,996,924
[45] Dec. 14, 1976

[54] OCCLUSIVE IMPEDANCE PHLEBOGRAPH AND METHOD THEREFOR

[76] Inventor: H. Brownell Wheeler, 540 Salisbury St., Worcester, Mass. 01609

[22] Filed: June 19, 1974

[21] Appl. No.: 481,115

[52] U.S. Cl. .................... 128/2.05 V; 128/2.1 Z
[51] Int. Cl.² .................................. A61B 5/02
[58] Field of Search ............. 128/2.05 V, 2.05 F, 128/2.05 R

[56] References Cited
UNITED STATES PATENTS

| | | | |
|---|---|---|---|
| 3,517,661 | 6/1970 | Buffington | 128/2.05 V |
| 3,545,430 | 12/1970 | Figar | 128/2.05 V |
| 3,698,382 | 10/1972 | Howell | 128/2.05 V X |
| 3,847,142 | 11/1974 | Williams, Jr. et al. | 128/2.05 F |
| 3,882,851 | 5/1975 | Sigworth | 128/2.05 V X |

OTHER PUBLICATIONS

Hokanson, D. E., et al., *IEEE Trans. on Bio-Engng.*, vol. BME-22, No. 1, Jan. 1975, pp. 25–29.
Jaffrin, M. Y., et al., *Digest of Conf. of 3rd Intern. Conf. on Med. Physics*, Goteborg, Sweden, 1972, (Wed. Aug. 2, A.M.) (p. 1).

*Primary Examiner*—Kyle L. Howell
*Attorney, Agent, or Firm*—Cesari and McKenna

[57] ABSTRACT

The venous patency of a human limb is assessed by measuring the venous outflow within a defined time interval after release of a forced blockage of the venous return to the heart and correlating it, where necessary, with the increased venous volume occasioned by the forced blockage. The volume changes and outflow rate are determined from electrical impedance measurements.

16 Claims, 5 Drawing Figures

OCCLUSIVE IMPEDANCE PHLEBOGRAPH AND METHOD THEREFOR

BACKGROUND OF THE INVENTION

A. Field of the Invention

The invention relates to medical diagnostics and, more particularly, to assessment of the venous circulation of human limbs, particularly the legs.

B. Prior Art

The human circulatory system is susceptible to numerous diseases and disorders. Frequently, these disorders manifest a defect in the circulatory system itself, while in other cases the disorder reflects a defect of primary origin elsewhere. In either case, it is desirable to be able to rapidly and accurately assess the functioning of the circulatory system of the patient.

The venous system of humans is particularly susceptible to seriously debilitating disorders arising from the gradual build-up of blood clots within the veins. In addition to obstructing the venous return to the heart, these clots sometimes reach a substantial size, break off, and then travel to the heart and lungs where they block circulation and frequently cause death. This complication can be prevented if clots are detected and appropriate treatment is scheduled. Thus, it is highly desirable to be able to determine whether one or more of these clots are present in the veins.

One technique I have heretofore utilized to assess venous patency is to measure the increase in venous volume accompanying a forced blockage of the venous return to the heart. This blockage may be applied by causing the patient to inhale deeply, thereby increasing intraabdominal pressure which in turn restricts venous return, or by applying a force to the venous system by means of devices such as a pressure cuff which collapses the veins and thereby blocks off the venous return. When the venous return is blocked in this manner, the veins accumulate the blood pumped into them from the arteries and store the excess blood by expanding their cross section to thereby increase the stored volume. The increase in blood volume (hereinafter termed "venous capacitance") is a measure of the distensibility of the veins and thus of the condition of the venous system.

Heretofore I have found that patients having a venous blockage such as is occasioned by a blood clot exhibit a noticably lower volume increase accompanying a forced blockage of the venous return than patients whose veins are normal. In particular, I measured the change in impedance through a portion of the limb being tested in response to a forced blockage of the venous return to the heart from that limb during deep breathing and compared it to the impedance measured when the patient was resting and absent any forced blockage, that is, the "resting baseline impedance." I found that patients exhibiting an impedance change of less than 0.2% of the resting baseline impedance in response to a forced blockage generally had one or more blood clots in their veins, while patients exhibiting an impedance change of greater than this amount were generally free of clots. This test has been extremely useful and beneficial; however, in certain cases it produces incorrect results. For example, a patient who is hypovolemic (that is, having a low blood volume) exhibits a low volume change on blockage of the venous return, thereby indicating a blood clot in the veins when actually none is present. Additionally, the measurements obtained frequently varied somewhat from observer to observer depending on judgemental factors of the observer in administering the test. Many sick or debilitated patients are unable to cooperate with the breathing maneuvers required. Thus, a test of greater accuracy and applicability is needed.

BRIEF DESCRIPTION OF THE INVENTION

A. Objects of the Invention

Accordingly, it is an object of the invention to provide an improved medical diagnostic method and apparatus.

Further, it is an object of the invention to provide an improved method and apparatus for assessing the functioning of the human venous system.

Another object of the invention is to provide a method and apparatus for quickly and accurately assessing the functioning of the human venous system.

Still a further object of the invention is to provide a method and apparatus for quickly and accurately detecting the presence or absence of a blood clot in the venous system.

B. Brief Summary of the Invention

In accordance with the present invention, I have found that the rate at which blood flows out from the venous system immediately following cessation of forced blockage of the venous return to the heart (hereinafter termed "venous outflow rate") is indicative of the functioning of the venous circulatory system. When correlated with the change in venous volume which accompanies the application of the force blockage (the venous capacitance), the venous outflow rate provides an accurate and reliable indication of the functioning of the venous system. Further, observation of changes in these measurements from one time period to another allows early diagnosis of venous circulatory system problems.

Both the venous outflow rate and the venous capacitance are measured by measuring the electrical impedance through the limb being tested. This is accomplished in a known manner by applying a current through a portion of the limb positioned between a first pair of current-applying electrodes and measuring the voltage drop occuring in this limb portion between two voltage-measuring electrodes positioned intermediate the current-applying electrodes. Typically, the voltage-measuring electrodes are positioned approximately 10 centimeters apart, and the current-applying electrodes are positioned adjacent them. Preferably, the limb through which the impedance is measured is elevated above the horizontal during these measurements so as to drain the pooled blood in the veins. Also, the limb is advantageously slightly bent so as to prevent inadvertent compression of the veins in the limb which occurs in some patients when the limb is fulled extended (straightened).

To begin the measurement, the impedance through a portion of the limb with the patient in a resting condition is established. This impedance is known as the "resting baseline impedance," $Z_o$; it provides a measure of the blood volume within the limb during the resting (normal) condition. Typically it is of the order of 40 ohms. The impedance changes hereafter described are expressed as a percentage of this impedance.

After the baseline impedance has been established the venous capcitance is measured by blocking off the venous return to the heart and measuring the resultant impedance change (in this case, a decrease) from the resting baseline impedance. The venous return may readily be blocked by causing the patient to breathe in deeply, but it is more advantageously accomplished by utilizing a pressure cuff placed around the limb and positioned between the limb portion to be tested and the heart. On inflation to a pressure greater than in the veins but less than in the arteries, the cuff collapses the veins and blocks off the venous return; the veins then accumulate (store) the blood pumped into them from the arteries in response to normal cardiac action.

In order to obtain accurate and repeatable measurements, the venous return should be blocked for a sufficient period of time to allow the veins to accumulate a substantial volume of excess blood in response to normal cardiac reaction. I have found that a period of 45 seconds is wholly adequate for most purposes, although it may sometimes be necessary to extend this time to periods of up to a minute and a half for patients with limited arterial input. Whatever the time interval utilized, the change in impedance from the resting baseline impedance over this interval is a direct measure of the venous capacity.

The venous outflow rate is next determined by releasing the venous blockage and measuring the impedance change over a suitably short time interval. Typically, over 80% of the excess blood volume in the veins will drain from the veins within approximately 3 seconds from the time of release of the blockage, absent a defect in the venous system; the remainder of the excess blood volume drains out at a slower rate. In venous systems which are obstructed by a blood clot, however, a substantially longer time interval is required to drain the venous system. Accordingly, the "short term" venous outflow rate (that is, the initial outflow rate following release of the venous blockage) constitutes a significant parameter for differentiating normal venous systems from abnormal venous systems.

The measurements required by the present invention may be performed in a variety of ways. Thus, they may be obtained from the tracings of a strip-chart recorder which continually traces the impedance through a limb section as the venous return from that limb is first blocked and then unblocked. Preferably, however, the measurements are obtained automatically; this not only facilitates the utilization of the testing procedure by unskilled and inexperienced personnel, but it also tends to insure uniformity and repeatability of the measurements. In apparatus in accordance with the present invention for automatically performing the measurements, the venous blockage is performed by means of a pressure cuff placed around the limb to be tested. The cuff is controlled by a timer circuit which causes the cuff to inflate and remain so for a predetermined time interval; energizes a measuring circuit to establish the impedance through the limb at the end of this time interval; causes the cuff to deflate; and energizes a second measuring circuit to determine the impedance change over a second time interval after deflation.

In one circuit performing these measurements, the difference between these impedances (that is, the venous outflow rate) is determined and compared with an index representative of the baseline impedance. As long as this difference is greater than this index, the circuit indicates the absence of blockage or constriction of the veins. I have found that a venous outflow rate of less than about 0.3% $Z_o$ per second (that is, about 0.12 ohms per second) nearly always indicates a venous constriction or blockage such as from a blood clot, while a venous outflow rate of greater than about 0.5% $Z_o$ per second (that is, about 0.20 ohms per second) nearly always indicates a healthy venous system.

Outflow rates within the range of from 0.3% $Z_o$ per second to 0.5% $Z_o$ per second are, by themselves, ambiguous. For venous outflow rates within this range, it is necessary to correlate the outflow rate with the measured venous capacity. Thus, a small venous outflow rate accompanied by a large venous capacitance is highly indicative of the presence of a clot or a constriction in the veins, while a small venous outflow rate accompanied by a small venous capcitance is quite likely to be normal.

The results of the measurements described herein may be presented in a variety of ways. When a simple "normal/abnormal" decision is desired, an automatic measuring circuit having a two-state output indicator such as a lamp, a buzzer, etc., may adequately display the measurement results. Alternatively, they may be plotted on a graph showing the venous outflow rate as a function of the venous capacitance; this allows rapid comparison with measurements of other patients and also facilitates comparison of subsequent measurements on the same patient. On such a chart, it will be found that measurements of a large number of patients not only tend to segregate themselves in distinct areas on the chart, depending on whether the patient's venous circulatory system is healthy or not, but also that the measurements in each segment tend to cluster around a regression line. Normally, this line has little significance for a "static" test, that is, a single measurement of the venous outflow rate and venous capacitance. However, as will be described more fully below, it has substantial significance with respect to repeated measurements over a time interval on the same patient.

The venous capacitance of patients often changes from day to day, we well as from time to time during the day, in response to changes in body metabolism, physiology, etc. When the venous capacitance changes, the venous outflow rate generally changes correspondingly. In patients with healthy venous circulation, the changes in venous capacitance and venous outflow rate generally bear a predetermined relationship to each other; experimentally, I have determined that these changes occur along a regression line defined by VOR = 0.59 (VC) (where VOR is the venous outflow rate and VC is the venous capacitance) in healthy circulatory systems, and along the line of much smaller circulatory systems which are constricted or blocked by a clot. Thus, by repeating measurements of venous outflow rate and venous capacitance on a patient, one can obtain an early indication of adverse changes in the venous circulatory system before these changes become significant enough to result in a measurement outside the normal range for a single measurement.

As an example of the results obtained with the present invention, in 113 patients examined for possible blockage of the major veins of the leg and proven not to have such blockage by other techniques (such as by venous phlebography), the present invention clearly indicated the lack of an obstruction in 117, an accuracy of approximately 96%. Rechecks of the patients showing abnormal measurements resulted in normal measurements, as may sometimes occur when the original test conditions induced error, e.g., by improper leg positioning or other such factors. Conversely, in 49 patients having proven recent clots in the popliteal, femoral, or iliac veins, the method of the present invention correctly diagnosed 48 as having a substantial blood clot, an accuracy of approximately 95%. in the 49th patient, the clot was in such a position (in the hypogastric vein and propagating into the common iliac vein) and of such a size (obstructing not more than 60% of the lumen) as not to be readily detectable by impedance techniques. Thus, the method has been proven accurate in detecting the presence of a fresh clot in the major veins of the leg in tests on 161 out of 166 patients. It should be noted the method of the present invention relies upon a noticable change in the hemodynamics of the venous system for detecting abnormalities. Thus, minor malfuctions in the system, such as the presence of small blockages of the calf veins, may not be detected. However, these disorders are not themselves dangerous, but become dangerous only as they enlarge and propagate into larger veins. As they enlarge these veins, they do indeed affect the hemodynamics of the venous circulatory system and thus are likely to be detected by the present invention.

DETAILED DESCRIPTION OF THE INVENTION

The foregoing and other and further objects and features of the invention will be more readily understood from the following detailed description of the invention when taken in conjunction with the accompanying drawings in which.

Figure 1:
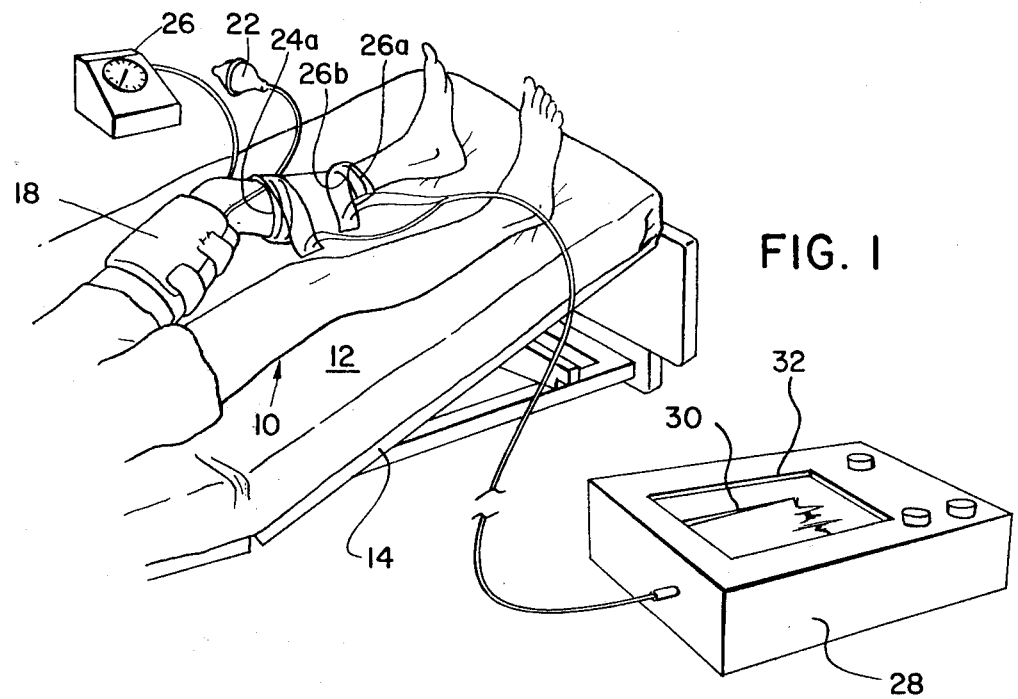
FIG. 1 is a pictorial view of a patient undergoing a test for venous patency of the left leg.

In FIG. 1 a patient 10 whose leg veins are to be tested for venous patency is positioned on a mattress 12 supported by frame 14 which elevates a leg 16 to be tested. Conveniently, the mattress 12 may be inclined at an angle of approximately 20° to the horizontal; elevating the mattress in this manner drains the pooled blood from the leg veins of the patient being tested, and assists in providing a standard reference for measurement of the desired circulatory parameters, that is venous capacitance and venous outflow rate. A pressure cuff 18 is positioned around the thigh just above the knee; it is connected to a sphygmomanometer 20 and is inflated by a squeeze bulb 22. Initially, the cuff is deflated.

Figure 2:
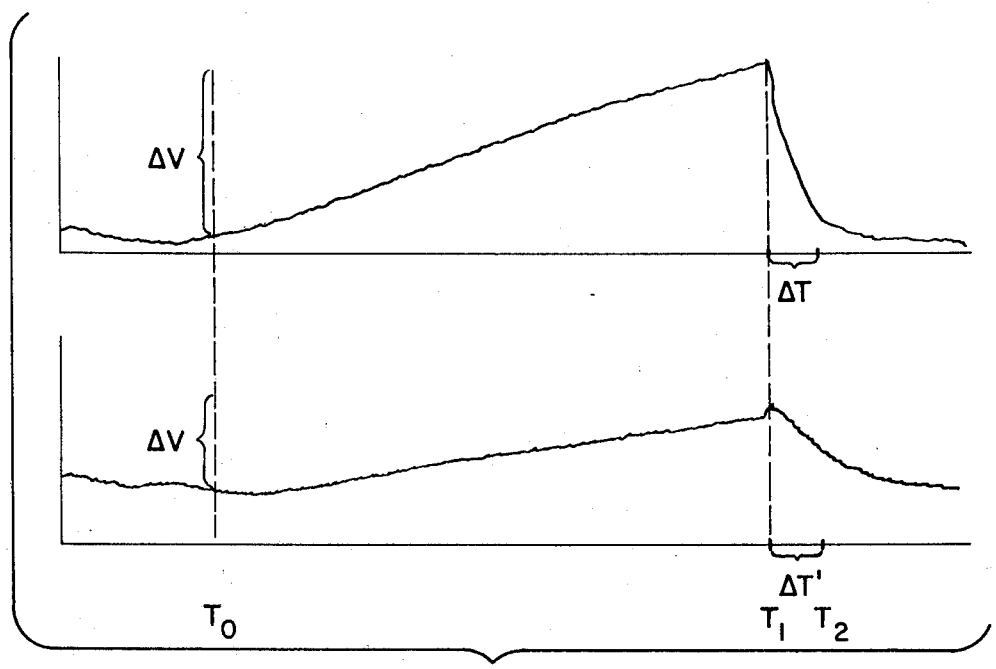
FIG. 2 is a reproduction of a tracing of the impedance through the limb of the patient in response to an initial blockage of the venous return to the heart and the subsequent release thereof.

A pair of electrode sets 24, 26 is positioned on the calf of the limb to be tested, and is connected to a measuring or recording instrument 28. The leg 16 is positioned to remove external forces which might constrict the veins or otherwise obstruct the venous return to the heart. For this purpose, the leg is slightly bent and the hip of the patient rotated slightly outwardly to relieve any longitudinal tension on the veins or any extraneous compression which might be applied to the veins by the bones of the knee joint. For purposes of illustration, the instrument 28 is depicted as a strip chart recorder having a laterally movable pen 30 which traces a record on a longitudinally movable chart 32. A typical record formed by such a recorder will be described in detail in connection with FIG. 2

The electrode pairs 24 and 26 each preferably consist of a pair of electrodes parallel to, and slightly spaced apart from each other. The outermost electrodes 24a and 26a drive a standardized high frequency, alternating current through the leg section between them, while the innermost electrodes 24b and 26b measure the voltage drop through the limb section in response to this current. The magnitude of the voltage and current define the impedance of the venous system of this leg section and this impedance is recorded by means of the recorder 28. The impedance is a function of the cross section of all the electrically conductive paths in the leg, including the arteries and veins. The conductivity of the arteries and veins changes with variations in blood volume, but the conductivity of all other electrically conductive paths remains essentially constant. Because of the substantially larger cross section of the veins as compared to the arteries, the changes in conductivity (and thus its reciprocal the impedance) due to blood volume changes is determined largely by the veins.

To begin the test, the impedance through the leg is first established with the patient in a resting condition; this is the resting baseline impedance. This impedance is of considerable magnitude (typically, approximately 40 ohms) in comparison to the magnitude of the impedance changes to be measured during the test (typically, tenths of ohms) and thus it is desirable to utilize an instrument establishing the resting baseline impedance as the "zero level" from which impedance changes are measured. An instrument which is specially suited for this purpose is the well known impedance bridge; when this bridge is set to balance at the resting baseline impedance, only the deviations from this impedance level are provided as output. Accordingly, in the discussion hereinafter, it will be assumed that the instrument 28 incorporates an impedance bridge such that it registers on the strip chart 30 only the deviations from the resting baseline impedance.

After the resting baseline impedance has been established, the venous return to the heart is blocked by inflating the pressure cuff 18 to an extent sufficient to collapse the veins and cut off the venous return. When this is done, the blood pumped into the veins of the leg from normal cardiac action accumulates in the veins, thereby increasing their cross section and decreasing the impedance measured through them. This change in impedance is shown clearly in FIG. 2 of the drawings in which an upper tracing, 32a, shows a typical impedance through the legs in response to the initial application, and subsequent release, of a forced blockage of the venous return in the leg of a patient having no malfunction of the venous system, (hereafter referred to as "normal") while the lower tracing, 32b, shows a typical impedance tracing under the same conditions in the leg of a patient having a venous clot (hereafter referred to as "abnormal"). In the drawings, a decrease in the impedance is represented by an upward excursion of the tracing, while an increase in impedance is represented by a downward excursion of this tracing. The scale is such that one vertical division (5mm on the recorder chart) equals 0.2% $Z_o$ where $Z_o$ is the resting baseline impedance which may vary from 20 to 90 ohms in extreme cases but typically is of the order of 40 ohms. One horizontal division equals 1.5 seconds.

The venous blockage is imposed at time $T_0$ and is maintained for an extended time until $T_1$. The time interval $T_1 - T_0$ should include a substantial number of cardiac cycles so that a substantial quantity of blood is pumped into the veins during this interval. In the tracings shown in FIG. 2, the blockage was maintained for a period of 45 seconds. During this time, the impedance through the normal leg dropped from $Z_0$ to $Z_1$, while the impedance through the leg containing a venous disorder dropped from $Z_0'$ to $Z_1'$. This corresponds to a volume increase of $\Delta V$, for the normal leg and $\Delta V'$, for the abnormal leg. In the examples shown in FIG. 2, the venous capacitance of the normal leg is approximately twice that of the abnormal leg.

At $T_1$ the cuff is deflated. In response to this, the leg veins begin to empty their stored excess blood volume and the impedance correspondingly increases toward the resting baseline impedance from FIG. 2. It will be noted that the normal leg empties its excess blood volume at a much faster initial rate than the abnormal leg; in the example shown, the initial outflow rate in the normal leg is approximately three and a half times the initial outflow rate in the abnormal leg. The initial outflow rate provides a significant measure to the patency of the venous system. This outflow rate is advantageously computed over a time interval of the order of approximately 3 seconds, an interval which is short enough to measure an outflow rate which is quite close to the maximum outflow rate throughout the interval, while long enough to provide a sufficient resolution to thereby insure accuracy and repeatability of the measurements.

Figure 3:
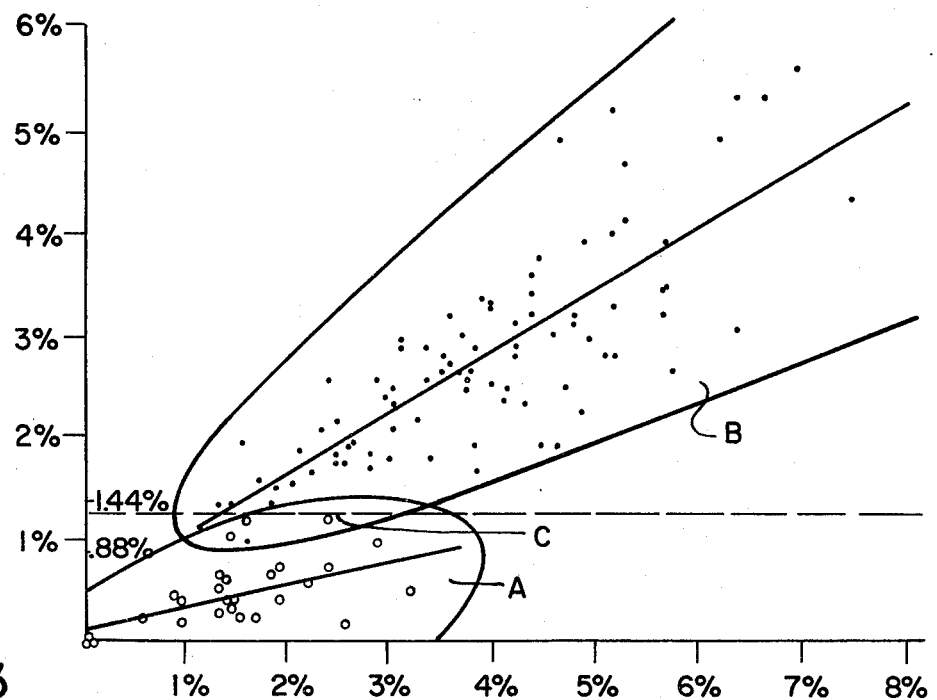
FIG. 3 is a diagram illustrating the relation between the venous outflow rate and venous capcitance and indicating the ranges of "normal" and "abnormal" with respect to substantial blood clots in the venous system.

Turning now to FIG. 3, a plot of the venous outflow rate (vertical scale, calibrated in percent of the patient's resting baseline impedance per three second interval) versus the venous capacitance (horizontal scale, calibrated in percent of the patient's resting baseline impedance is shown). The closed dots represent measurements of impedance through the legs of patients in which the absence of any venous restrictions or clots was independently confirmed by other methods; the open dots represent measurements of impedance through legs of patients in which the presence of a venous clot or restriction was independently confirmed by other methods.

It will be seen from FIG. 3 that the normal measurements (those indicating the absence of a venous disorder) group themselves into a generally separable region of the graph from the abnormal measurements (those indicating a venous disorder, in this case, a blood clot). For example, one may demarcate the two groups by enclosing them within separate generally smooth contours, each encompassing all the points within one group and as few as possible points from the other group. In FIG. 3, such contours are shown enclosing the abnormal region designated "A" and the normal region designated "B." This creates a zone of ambiguity, designated "C" in FIG. 3, which contains three abnormal and one normal measurement. Within these zones the normal measurements cluster along a regression line 40 given by $VOR = (0.59 \, VC + .48)\%$ per 3 second interval, while the abnormal measurements cluster along a line given by $VOR = (0.23 \, VC + 0.14)$ percent per 3 second interval.

Alternatively, it will be noted that a horizontal line at approximately 1.2% $Z_0$ per 3 second interval (that is, 0.4% $Z_0$ per second, where $Z_0$ is the resting baseline impedance) distinguishes most normal measurements from abnormal measurements, and incorrectly categorizes only a single measurement. An uncertainty zone of from 1.0% to 1.4% per 3 second period may desirably be provided for in which all measurements are confirmed by repetition. Thus, the venous outflow rate provides an index of substantial sensitivity to help distinguish normal measurements from abnormal measurements. However, the venous outflow rate may vary considerably from patient to patient, as well as from time to time in a patient depending on the patient's venous capacitance. Thus, comparison of the venous outflow rate with the venous capacitance provides a more reliable indicator of the functioning of the venous system.

This is especially the case when measurements on a particular patient are repeated over a period of time and a history of the changes in these measurements is followed. In these situations it will be found that the venous outflow rate changes quite rapidly with changes in venous capacitance in patients with incipient disorders of the circulatory system (e.g., as shown by the rectangles in FIG. 3 in a hypothetical case) and changes less rapidly with changes in venous capacitance in normal patients (e.g., as shown by the triangle in FIG. 3 in a further hypothetical case). Indeed, the latter changes typically occur along lines parallel to the regression line 40 of FIG. 3. Thus, repeated observation on the same patient can provide early diagnosis of incipient circulatory disorders which are not yet of a magnitude sufficient to depart from the normal regions of FIG. 3.

Figure 4:
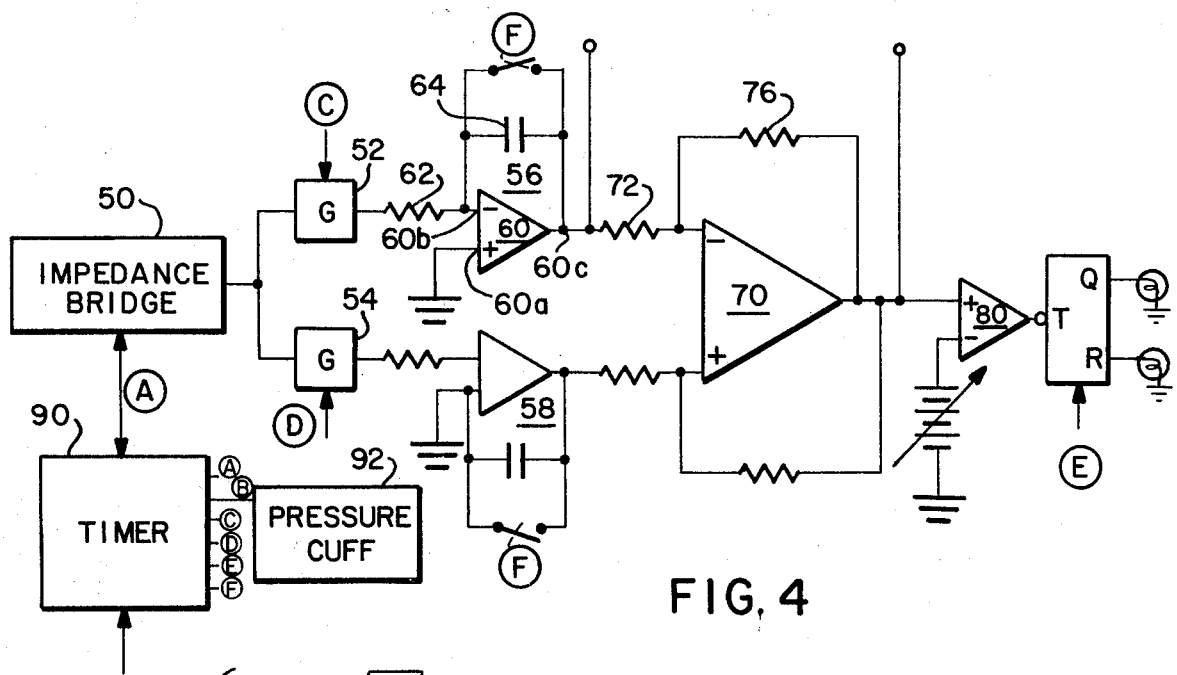
FIG. 4 is a circuit diagram accompanied by a timing diagram of one apparatus for measuring the venous outflow rate alone.

Turning now to FIG. 4, there is shown a circuit for automatically measuring the venous outflow rate and venous capacitance over a defined time interval and comparing them with a selected index. The circuit comprises an impedance bridge 50 connected through gates 52 and 54 to sample and hold circuits 56 and 58. The bridge 50 is balanced to the patient's resting baseline impedance at the start of the test. A typical sample and hold circuit 56 comprises an amplifier 60 having the conventional inverting and non-inverting input terminals 60a and 60b, respectively; a resistor 62 connected to the inverting input terminal 60b; a ground lead connected to the non-inverting input terminal 60a; a capacitor 64 connected between the inverting input terminal and the output terminal; and a switch 66 connected across the capacitor. The amplifier 60 is a high gain, high input impedance, low output impedance ("operational") amplifier and the time constant of the R-C combination of resistor 62 and capacitor 64 is low to minimize sampling errors. The sample and hold circuit 58 is similarly constructed and it will not be described in detail.

The outputs of the circuits 56 and 58 are applied to the inverting and non-inverting inputs, respectively, of an operational amplifier 70 through resistors 72, 74, respectively. Feedback resistors 76, 78 are connected between the output terminal of amplifier 70 and the corresponding input terminals and determine the gain of the amplifier from the input terminals thereof to the output terminals in combination with the resistors 72 and 74. For reasons described below, this gain is set to a value of $k$, where $k$ is the index (here, 1.2% $Z_0$ per 3 second interval) separating normal from abnormal outflow rates. The output of the amplifier 70 is applied to the noninverting input of an operational amplifier 80 which serves as a comparator; a reference voltage corresponding to the impedance $Z_{0s}$ (for purposes of illustration, shown as a battery 82) is applied to the inverting input thereof. The comparator 80 drives the toggle input of a flip flop 82 which is normally in the reset state. It is changed from this state only if the toggle input is positive at the time it is strobed at its strobe terminal 82a. The Q output of the flip flop drives an indicator lamp 84; similarly, the R output drives a lamp 86. The circuit also includes a timer 90 which controls the measurements made by the circuit, and a pressure cuff 92 corresponding to cuff 18 of FIG. 1 and including inflation means (e.g., a source of compressed air and an electronic valve connecting the air to the cuff when open and venting the cuff to atmosphere when closed) which is inflated in response to a signal from timer 90 and deflated thereafter.

Figure 5:
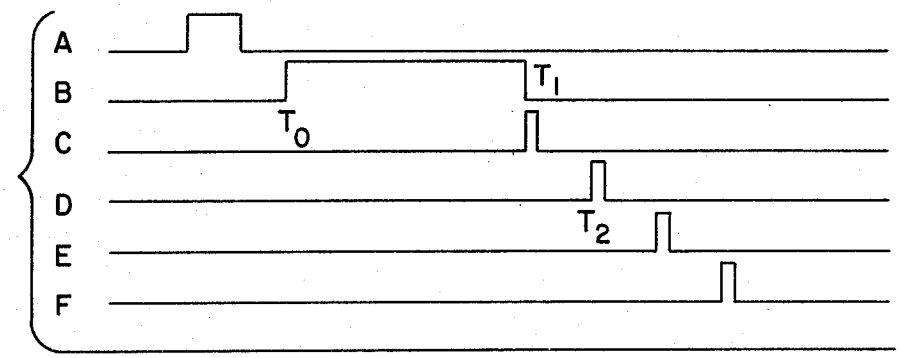
FIG. 5 is a circuit diagram, accompanied by a timing diagram, of an apparatus for measuring the venous outflow rate as well as venous capacitance and comparing the two.

Referring now to FIG. 5 in conjunction with FIG. 4, the test is begun by setting bridge 50 to the resting baseline impedance of the patient whose venous system is being tested. Preferably this is accomplished automatically by the bridge 50 in response to a control signal emitted by timer 90 and shown as signal "A" in FIG. 5. Thereafter, bridge 50 tracks the impedance excursions from the patient's resting baseline impedance. After this is accomplished, the timer 90 applies to cuff-inflation signal (signal "B" in FIG. 4A) to pressure cuff 92 to cause this cuff to inflate and remain in the inflated state for the duration of the signal; this blocks the venous return to the heart. For the reasons previously described, this signal should have a duration of the order of 45 seconds or more in order to insure a substantial distention of the veins.

At the end of the inflation period, and immediately before the pressure cuff 92 is deflated, the timer 90 emits a measurement signal (designated "C" in FIG. 5) which opens gate 52 and connects the sample and hold circuit 56 to the impedance bridge 50. The duration of the sampling signal C should only be long enough to allow the sample and hold circuit 56 to obtain an accurate indication of the impedance $Z_1$ measured by the bridge 50 at the time the sampling signal is generated. The sample and hold circuit 56 samples the instantaneous magnitude of the impedance measured by the bridge (which is actually the impedance change from the patient's resting baseline impedance) and provides as output a voltage indicative of this magnitude. This voltage is held for subsequent processing.

At a defined time after the end of the cuff inflation signal B (FIG. 5) and thus the end of the first measurement, the timer 90 emits a second measurement signal D (FIG. 5) which opens gate 54 and connects sample and hold circuit 58 to impedance bridge 50. This event occurs at a timer $T_2$ which is preferably approximately 3 seconds after the deflation of the pressure cuff. The sample and hold circuit 58 registers the impedance $Z_2$ measured by bridge 50 at the time $T_2$ and provides an output voltage indicative of this value. The scaled difference $1/K (Z_2 - Z_1)$ is formed by the amplifier 70 and applied to the comparator 80 where its magnitude is compared with the magnitude of the index established by battery 82. If the impedance difference is greater than the index, that is, if $1/k (Z_2 - Z_1) > Z_{ox}$ and thus $(Z_2 - Z_1) > k Z_{ox}$ where $k$ is approximately 1.2, the output of amplifier 80 is highly positive and the flip-flop 82 lights lamp 84 when it is strobed by strobe signal E emitted by timer 90. This indicates a normal venous system. Conversely, if the impedance difference is less than the index established by battery 82, the output of the amplifier 80 is highly negative and flip flop remains in the reset state when strobed. Thus, lamp 86 lights to indicate an abnormal venous system. The system is reset in response to timing signal F(FIG. 5) which dumps the capacitors of the sample and hold circuits 56 and 58 by closing the shorting switches across them.

Numerous alternatives for carrying out the tests described herein will suggest themselves to those of ordinary skill in the art. For example, the venous outflow rate and venous capacitance may be measured by techniques other than electrical impedance techniques. For example, limb volume changes may be measured pneumatically or hydraulically and the pneumatic or hydraulic analagy to FIG. 3 may be established to determine the corresponding index for assessing venous patency. Similarly, a function generator maybe employed to simulate the areas designated A and B in FIG. 3 for testing measured values of the various measurements of venous outflow and venous capacitance to determine whether the measurements lie within the normal or the abnormal range. Other modifications will suggest themselves to those or ordinary skill in the art in carrying out the method in the present invention.

SUMMARY

From the foregoing, it will be seen that I have described a method and apparatus for accurately and rapidly assessing the patency of the venous system and, in particular, that of the major veins (popliteal, femoral, and iliac) of the venous system in the lower limb. The method is simple to utilize, quickly performed, and highly accurate. Apparatus is also provided for performing the measurements and registering the results.

Having illustrated and described my invention, I claim:

1. A method of assessing the patency of the venous system in an animal body limb, comprising the steps of
   A. blocking off the venous return to the heart from the limb to be tested,
   B. maintaining said blockage for a period of time sufficient to accumulate excess blood in said limb portion,
   C. releasing said blockage and measuring the rate of venous outflow from said limb occurring within a defined time interval in response to said release, and
   D. registering said system as healthy when said rate is greater than the rate defined by (0.60 VC + 0.48), where VC is the venous capacitance, and registering said limb as diseased when said rate is less than the rate defined by (0.20 VC + 0.14).

2. A method according to claim 1 in which said blockage is maintained for a period equal to a substantial number of cardiac cycles.

3. A method according to claim 2 in which said blockage is maintained for a period in excess of 30 seconds.

4. A method according to claim 1 in which the defined time interval over which the outflow rate is measured is small compared to the time during which the blockage is maintained.

5. The method of claim 4 in which the defined time interval is less than 5 seconds.

6. The method of claim 5 in which the defined time interval is approximately 3 seconds.

7. The method of claim 1 which includes the steps of draining blood from the limb prior to imposing a blockage therein.

8. The method of claim 7 in which said drainage is accomplished by elevating the limb above the horizontal.

9. The method of claim 8 in which said limb is blocked by applying a pressure cuff to the limb at a position intermediate the heart and that portion of the limb to be tested and thereafter inflating said cuff to thereby block off the venous return to the heart.

10. The method of claim 9 in which said limb comprises a leg and in which the pressure cuff is placed immediately above the knee on the leg.

11. The method of claim 1 in which the rate of venous outflow is measured by measuring the rate of change of electrical impedance between at least two electrodes placed on the limb portion to be tested.

12. The method of claim 11 in which the absence of a venous blood clot is to be determined and the range of rates to which the venous outflow rate is compared comprises those rates corresponding to electrical impedance changes of approximately 0.4% $Z_o$ per second.

13. The method of claim 11 in which the pressure of a venous blood clot is to be determined and the range of rates to which the venous outflow rate is compared comprises those rates corresponding to electrical impedance changes of approximately 0.4% $Z_o$ per second or less.

14. The method of claim 1 which includes the steps of measuring the venous capacitance in response to the forced blockage and comparing it to the venous outflow rate following release of said blockage, a measurement of venous capacitance and venous outflow rate lying within the region labelled "A" in FIG. 3 indicating a venous blockage and a measurement of the quantities lying within region "B" of FIG. 3 indicating absence of such blockage.

15. Apparatus for assessing the patency of the veins in an animal body limb comprising:
  A. means for measuring the venous outflow from said limb during a given time interval following release of a forced blockage of the venous return to the heart and,
  B. means responsive to the measured outflow to provide an output indicative of whether or not said outflow is less than the rate defined by (0.20 VC + 0.14) where VC is the venous capacitance.

16. Apparatus according to claim 15:
  1. including means for measuring a increase in venous volume following said venous blockage; and
  2. in which said indicating mean is responsive to said increase measuring means to indicate whether both the increase and decrease bear a defined relationship to each other.

* * * * *